United States Patent

Ruess

[11] Patent Number: 5,582,181
[45] Date of Patent: Dec. 10, 1996

[54] DEVICE AND A METHOD FOR EQUALIZING A PATIENT'S POTENTIAL WITH RESPECT TO MEDICAL EQUIPMENT

[75] Inventor: Martin Ruess, Boeblingen, Germany

[73] Assignee: Hewlett-Packard Company, Palo Alto, Calif.

[21] Appl. No.: 444,222

[22] Filed: May 18, 1995

[30] Foreign Application Priority Data

Sep. 10, 1994 [DE] Germany .......................... 94114250.7

[51] Int. Cl.⁶ .................................................. A61B 5/0402
[52] U.S. Cl. .......................... 128/696; 128/901; 128/905
[58] Field of Search ..................... 128/695, 696, 128/731–733, 901, 902, 905, 908; 607/28, 63; 364/413.05, 413.06

[56] References Cited

U.S. PATENT DOCUMENTS

| | | | |
|---|---|---|---|
| 3,602,215 | 8/1971 | Parnell | 128/902 X |
| 3,623,477 | 11/1971 | Trent . | |
| 4,890,630 | 1/1990 | Kroll et al. | 128/905 X |
| 5,016,635 | 5/1991 | Graupe | 128/733 X |
| 5,020,541 | 6/1991 | Marriott | 128/696 X |
| 5,392,784 | 2/1995 | Gudaitis | 128/696 |
| 5,427,110 | 6/1995 | Danielsson | 128/696 |

FOREIGN PATENT DOCUMENTS

| | | |
|---|---|---|
| 0182197A3 | 5/1986 | European Pat. Off. . |
| 0335977A1 | 10/1989 | European Pat. Off. . |

Primary Examiner—Jeffrey R. Jastrzab

[57] ABSTRACT

A device for equalizing a patient's potential with respect to medical equipment, in particular upon recording an electrocardiogram, includes at least two measuring electrodes and a reference electrode which are adapted to be applied to the patient, a drive-signal generation circuit having its output side connected to said reference electrode, a control circuit which has supplied thereto the measuring signals from said measuring electrodes and which examines whether the measuring signals lie within a predetermined range, said control circuit supplying said measuring signals to inputs of the drive-signal generation circuit, if said measuring signals lie within a predetermined range. The device according to the present invention and the method according to the present invention prevent measuring electrodes which are not adequately fixed or which do not function properly from being used for forming the drive signal which is applied to the reference electrode so that disturbances caused by the malfunctioning electrode will not be coupled into the patient and will, consequently, not have a disadvantageous influence on the measuring signals of the other electrodes either.

7 Claims, 4 Drawing Sheets

1

DEVICE AND A METHOD FOR EQUALIZING A PATIENT'S POTENTIAL WITH RESPECT TO MEDICAL EQUIPMENT

FIELD OF THE INVENTION

The present invention discloses a device and a method for equalizing a patient's potential with respect to medical equipment, in particular upon recording an electrocardiogram.

DESCRIPTION OF THE PRIOR ART

The prior art already discloses devices for potential equalization, so-called "right leg drive" systems (right leg drive= drive circuit for the right leg). FIG. 4 and 5 (wherein corresponding parts have been given the same reference signs) show a known electrocardiogram measuring instrument 400 comprising a plurality of electrodes 401–405 which are applied to a patient. In order to prevent the patient 406 from being endangered by leakage or equalization currents when the measured values of the electrocardiogram are recorded, the whole measurement sensor is galvanically separated from its environment. In this known system, this galvanic separation is effected by a transformer 408 by means of which the measurement sensor is galvanically separated from a power supply 410 or a battery. The power supply 410 is connected to the protective earthing 412.

It is evident that the potential 414 of the measurement sensor is thus not defined with respect to its environment and especially with respect to the protective earthing 412.

In view of the fact that the measurement sensor has a restricted common mode rejection, a potential equalization of the patient 406 with respect to the insulated measurement sensor must be effected through one or several of the electrodes 401–405, so called reference electrodes, in this case through reference electrode 404.

In view of the fact that the reference electrode 404 is normally connected to the patient's right leg, the name "right leg drive" (RLD) has come into use.

In this known measuring instrument, as shown in FIG. 4, a so called passive equalization is carried out, wherein the reference electrode 404 is in this case fixedly connected to the reference ground 414 of the insulated measurement sensor.

In order to improve the common mode rejection of electrode displacement voltages and mains disturbances, i.e. of disturbances at 50 or 60 Hz, a measurement instrument as shown in FIG. 5 is used, which carries out a so called active equalization.

In this instrument the reference electrode 404 is connected to an output of a drive-signal generation circuit 518 whose inputs are connected to the rest of the electrodes 401, 402, 403, 405 and to the reference ground 414 of the insulated measurement sensor. Due to this connection of the electrodes to the drive-signal generation circuit 518, the electrocardiogram signal detected by the measuring electrodes is reverse coupled to the reference electrode 404 as a drive signal, whereby the common mode control of the measurement sensor is equalized.

The electrocardiogram measuring instrument 400 (see FIG. 4 or FIG. 5) additionally includes a vector calculation unit 420 for producing a vector by a weighted summation of the measuring electrode potentials so as to define a channel. Depending on the presetting of the electrocardiogram measuring instrument 400, a predetermined number of vectors and, consequently, a predetermined number of channels is produced by the vector calculation unit 420.

The vector calculation unit 420 is also connected to the reference ground 414 of the measurement sensor. The patient 416 is coupled to ground 412 via a normally undefined impedance Z.

The active equalized system described in FIG. 5 has, however, some disadvantages.

In particular, it may happen that the measuring electrodes 401, 402, 403, 405 acquire a very high resistance due to falling off, drying out, or due to not being properly applied. As a result, disturbances are coupled in, which will influence or even swamp the electrocardiogram signal. This applies to all channels in connection with which these high ohmic electrodes are used for a weighted formation of the vectors.

If the malfunctioning, high ohmic electrode is used for contributing to the drive signal, these disturbances will be coupled into the patient 406 via the reference electrode 404. Hence, it is clearly evident that a single malfunctioning measuring electrode will interfere with all the other measuring electrodes.

This applies especially also to channels which do not use any of the high ohmic, malfunctioning electrodes for the purpose of vector formation.

This problem is made clear by the diagram shown in FIG. 3a. Signal waveform 300 corresponds, for example, to a first channel, which is composed of electrodes 405 and 401.

Signal waveform 302 corresponds to a second channel, which is composed of the measuring signals of electrodes 405 and 402.

After a period of time t1, a disturbance occurs at electrode 401; electrode 401 may, for example, fall off, and, as a result, a signal will no longer be transmitted, as can be seen in section 304 of the signal waveform 300.

In view of the fact that the measuring signal of the malfunctioning measuring electrode 401 is used for generating the drive signal applied to reference electrode 404, a disturbance will also occur in the second channel 302, although this channel does not even use the malfunctioning measuring electrode 401.

This is due to the fact that the faulty measuring signal of electrode 401 is coupled into the patient 406 via the drive-signal generation circuit 518 and via the reference electrode 404, and, consequently, said faulty measuring signal will affect the second channel. As can be seen from section 306 of the signal waveform 302, this will have the effect that e.g. mains disturbances are coupled in, which swamp the measuring signal and which make it therefore impossible to record said measuring signal.

U.S. Pat. No. 4,577,639 discloses a device and a method for an automatic selection of measuring electrodes in the field of electrocardiography. This device comprises measuring electrodes which are connected to an electrode malfunction examination circuit, the electrodes being connected to a central calculation unit and an insulated electrocardiogram preprocessor for said examination circuit.

This known device uses a central processing unit for automatically selecting an electrocardiogram measuring electrode configuration in which all electrodes are applied to the patient and are below an impedance threshold. If the measuring electrode malfunction examination circuit detects that one or more electrocardiogram measuring electrodes do not function properly, the central processing unit will select a different configuration which does not include any malfunctioning electrocardiogram measuring electrodes.

U.S. Pat. No. 4,577,639 does not disclose any potential equalization of a patient with respect to the measurement sensor.

SUMMARY OF THE INVENTION

It is therefore a major object of the present invention to provide a device and a method which do not use faulty electrode signals for the purpose of producing a drive signal for a reference electrode so that these disturbances are prevented from being coupled into the patient and so that the properly functioning electrodes will still be used for the formation of valid vectors.

In accordance with a first aspect of the invention, this object is achieved by a device for equalizing a patient's potential with respect to medical equipment, in particular upon recording an electrocardiogram, comprising:

a measuring electrode and a reference electrode, which are adapted to be applied to the patient;

a drive-signal generation circuit having its output side connected to the reference electrode; and a control circuit which has supplied thereto a measuring signal from said measuring electrode and which examines whether said measuring signal lies within a predetermined range, said control circuit supplying the measuring signal to an input of the drive-signal generation circuit if said measuring signal lies within a predetermined range; and said control circuit applying a reference potential to the input of the drive-signal generation circuit if said measuring signal does not lie within said predetermined range.

In accordance with a second aspect of the invention, this object is achieved by a device for equalizing a patient's potential with respect to medical equipment, in particular upon recording an electrocardiogram, comprising:

at least two measuring electrodes and one reference electrode which are adapted to be applied to the patient;

a drive-signal generation circuit having its output side connected to the reference electrode;

a control circuit which has supplied thereto the measuring signals from said measuring electrodes and which examines whether said measuring signals lie within a predetermined range;

said control circuit supplying only those measuring signals to inputs of the drive-signal generation circuit which lie within a predetermined range.

In a preferred embodiment of the invention, the control circuit applies a reference potential to an input of the drive-signal generation circuit if the measuring signals do not lie within said predetermined range.

In another preferred embodiment of the invention, the device for equalizing a patient's potential with respect to medical equipment additionally comprises a device combining the measuring signals so as to form a single or a plurality of vectors for defining thus channels, the control circuit supplying to said drive-signal generation circuit only measuring signals which are included in one or more of these vectors.

In another preferred embodiment of the invention, the drive-signal generation circuit includes at least two switches on the input side by means of which the measuring signals can selectively be supplied to the inputs of said drive-signal generation circuit; wherein the control circuit comprises an analog-to-digital converter, a central processing unit and a switch control means;

said analog-to-digital converter is connected to the measuring electrodes and the reference electrode and, via a first signal bus, to the central processing unit;

the central processing unit is connected via a second signal bus to the switch control means, which, in turn, switches the input-side switches in response to control signals received.

In a further preferred embodiment of the invention, the drive-signal generation circuit includes an input-side reference potential switch by means of which a reference potential can be applied to said drive-signal generation circuit.

In accordance with a third aspect of the invention, this object is achieved by a method for equalizing a patient's potential with respect to medical equipment, in particular upon recording an electrocardiogram, comprising the following steps:

applying a measuring electrode and a reference electrode to the patient;

examining whether a measuring signal supplied by the measuring electrode lies within a predetermined range;

producing a drive signal, which is supplied to the reference electrode, on the basis of the measuring signal, if said measuring signal lies within said predetermined range; and applying a reference potential to the reference electrode, if said measuring signal does not lie within said predetermined range.

In accordance with a fourth aspect of the invention, this object is achieved by a method for equalizing a patient's potential with respect to medical equipment, in particular upon recording an electrocardiogram, comprising the following steps:

applying at least two measuring electrodes and a reference electrode to the patient;

examining whether the measuring signals supplied by the measuring electrodes lie within a predetermined range; and producing a drive signal, which is supplied to the reference electrode, only on the basis of the measuring signals which lie within said predetermined range.

In a further preferred embodiment of the invention, the method further comprises the step of:

applying a reference potential to the reference electrode, if the measuring signals do not lie within said predetermined range.

Thus, the present invention provides a device for equalizing a patient's potential with respect to medical equipment, in particular upon recording an electrocardiogram, said device comprising a measuring electrode and a reference electrode, which are adapted to be applied to a patient, a drive-signal generation circuit having its output side connected to the reference electrode, and a control circuit which has supplied thereto a measuring signal from said measuring electrode and which examines whether said measuring signal lies within a predetermined range, said control circuit supplying the measuring signal to an input of the drive-signal generation circuit if said measuring signal lies within a predetermined range, and said control circuit applying a reference potential to the input of the drive-signal generation circuit if said measuring signal does not lie within said predetermined range.

The present invention provides a device for equalizing a patient's potential with respect to medical equipment, in particular upon recording an electrocardiogram, said device comprising at least two measuring electrodes and one reference electrode, which are adapted to be applied to a patient, a drive-signal generation circuit having its output side connected to the reference electrode, a control circuit which has supplied thereto the measuring signals from said measuring electrodes and which examines whether said measuring signals lie within a predetermined range, said control circuit supplying the measuring signals to inputs of the drive-signal generation circuit if said measuring signals lie within a predetermined range.

The present invention provides a method for equalizing a patient's potential with respect to medical equipment, in particular upon recording an electrocardiogram, said method comprising the following steps: applying a measuring electrode and a reference electrode to the patient; examining whether a measuring signal supplied by the measuring electrode lies within a predetermined range; producing a drive signal, which is supplied to the reference electrode, on the basis of the measuring signal, if said measuring signal lies within said predetermined range; and applying a reference potential to the reference electrode, if said measuring signal does not lie within said predetermined range.

The present invention provides a method for equalizing a patient's potential with respect to medical equipment, in particular upon recording an electrocardiogram, said method comprising the following steps: applying at least two measuring electrodes and a reference electrode to the patient; examining whether the measuring signals supplied by the measuring electrodes lie within a predetermined range; producing a drive signal, which is supplied to the reference electrode, only on the basis of the measuring signals which lie within said predetermined range.

An advantageous aspect of the present invention is to be seen in the fact that a continuous supervision of the patient is still possible if one electrode does not work properly, especially when several channels are evaluated in parallel.

BRIEF DESCRIPTION OF THE DRAWINGS

A preferred embodiment of the present invention will be explained in detail hereinbelow on the basis of the drawings enclosed, in which.

DESCRIPTION OF THE PREFERRED
EMBODIMENTS OF THE INVENTION

Figure 1:
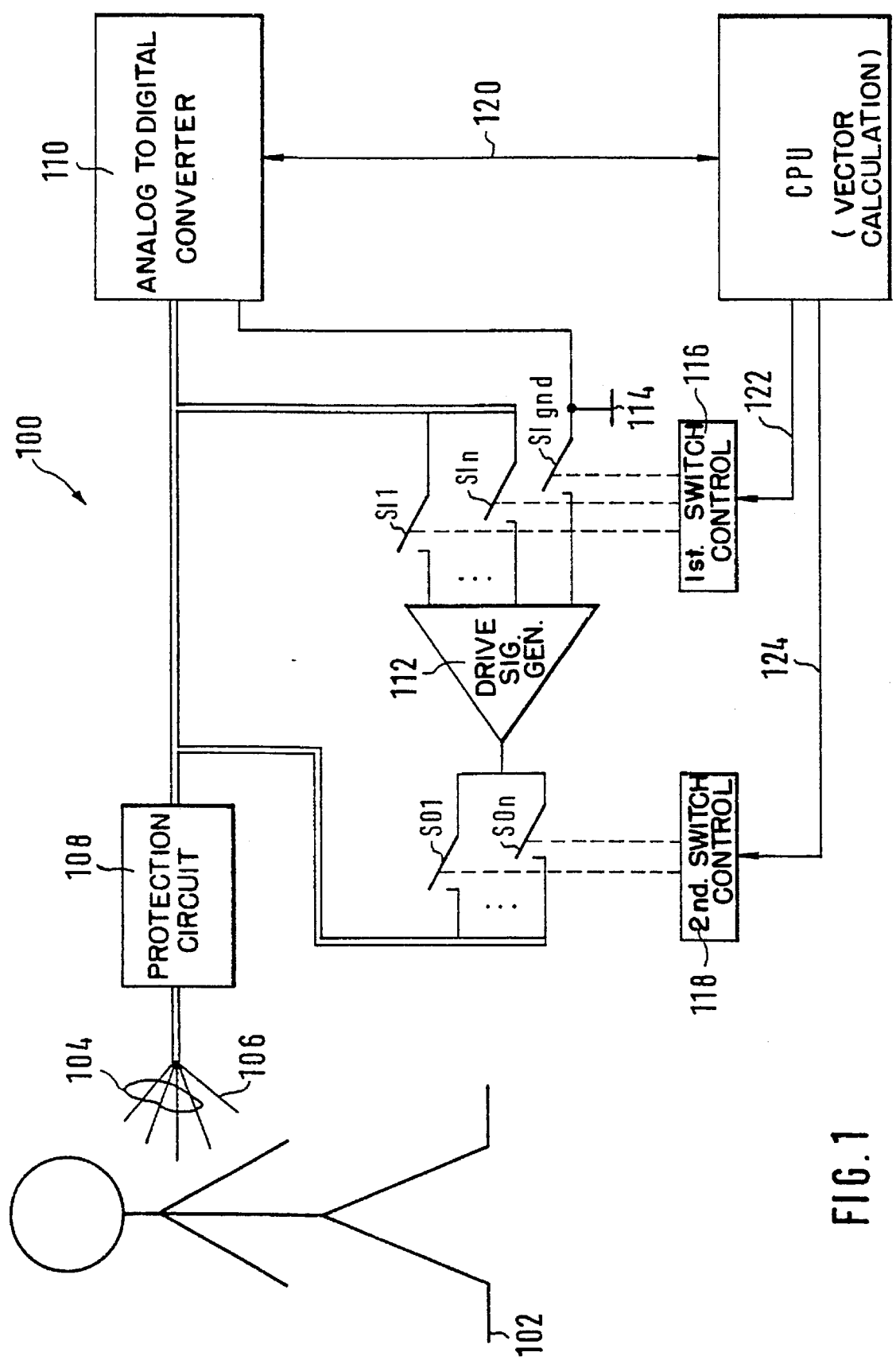
FIG. 1 shows a block diagram of the embodiment of the present invention.

FIG. 1 shows an embodiment of the device according to the present invention, which is used for equalizing a patient's potential with respect to medical equipment.

FIG. 1 shows a measurement sensor 100 and a patient 102, said measurement sensor defining part of an electrocardiogram measuring instrument and being galvanically decoupled therefrom. The measurement sensor 100 comprises a plurality of measuring electrodes 104 as well as one or several reference electrodes 106.

The measuring electrodes 104 are applied to the patient 102, and the reference electrode 106 is preferably applied to the patient's right leg. The electrodes 104, 106 are connected to an analog-to-digital converter 110 via a filter and protection circuit 108.

The measuring electrodes 104 are additionally connected to the inputs of a drive-signal generation circuit 112 via a plurality of switches SI1–SIn. The output of the drive-signal generation circuit 112 is connected to the reference electrodes 106 via switches SO1–SOn.

It is clearly evident that the number of switches SI1–SIn and SO1–SOn used depends on the number of measuring electrodes 104 and reference electrodes 106 used.

The drive-signal generation circuit 112 is provided with a switch SIgnd, which is located at an additional input thereof and which is connected to the reference ground 114 of the measurement sensor. Control of the various switches SI1–SIn, SIgnd, is effected via a first switch control means 116, whereas control of the switches SO1–SOn is effected via a second switch control means 118.

It is noted that the above described components, 110, 112, 116, 118, SOi, SIi, SIgnd may be integrated in one or more physical devices.

The analog-to-digital converter 110 is connected via a first signal bus 120 to a central processing unit CPU, which, in turn, transmits control signals to the first switch control means 116 via a second signal bus 122 and control signals to the second switch control means 118 via a third signal bus 124. The analog-to-digital converter 110 is further connected to the reference ground 114 of the measurement sensor.

It is noted that the signal busses 120, 122, 124 may be implemented as only one bus.

In the embodiment of a measurement sensor 100 shown in FIG. 1, the analog-to-digital converter 110, the CPU and the two switch control means 116, 118 with their associated switches SI1–SIn, SIgnd, SO1–SOn constitute a control circuit.

This control circuit, which receives (in the analog-to-digital converter 110) measuring signals of the measuring electrodes, examines whether these measuring signals lie within a predetermined range. Depending on the result of this examination, the control circuit controls via the first switch control means 116 the switches, which are associated with said switch control means 116, in such a way that the input of the drive-signal generation circuit 112 will have has supplied thereto a measuring signal only if said measuring signal lies within said predetermined range.

If all the measuring signals examined lie outside of said predetermined range, no measuring signal will be applied to the drive-signal generation circuit 112, i.e. the switches SI1–SIn are open, and the reference electrode 106 has applied thereto the reference potential 114 of the measurement sensor 100 via the drive-signal generation circuit 112, i.e. the switch SIgnd is closed.

The measurement sensor 100 additionally includes a device (not shown) combining the measuring signals so as to form a vector. In one embodiment of the present invention this combination may be done within the CPU. If this is the case, the control circuit is adjusted such that the drive-signal generation circuit 112 will have supplied thereto only measuring signals which are included in said vector.

It is clearly evident that it is just as well possible to define a plurality of channels so that, in this case, the control circuit will only supply measuring signals which are defined in one or more of said channels to the drive-signal generation circuit.

Furthermore, the control circuit will not supply to the drive-signal generation circuit 112 any signals of measuring electrodes which are used not only for the purpose of electrocardiogram detection but also for other purposes, e.g. resistance measurement.

Deviating from the embodiment described hereinbefore, it is also possible to provide a plurality of reference electrodes 106.

In addition, it is also possible to adjust the configuration of the measuring electrodes 104 and of the reference electrodes 106. In this case, the switches SO1–SOn are provided at the output of the drive-signal generation circuit 112.

A selection is carried out by not closing on the input side of the drive-signal generation circuit 112 the switches associated with the selected reference electrodes and by simultaneously closing on the output side of the drive-signal generation circuit 112 the switches corresponding to these predetermined electrodes, the rest of the switches on the output side of the drive-signal generation circuit 112 remaining open. This permits the electrodes used to be freely assigned as measuring electrodes 104 or as reference electrodes 106.

In accordance with an additional deviation of the embodiment described hereinbefore, only one measuring electrode 104 and one reference electrode 106 can be used instead of the plurality of electrodes (measuring or reference electrodes).

In this case, only three switches SI1, SI2, SIgnd are necessary at the input of the drive-signal generation circuit 112 and only two switches SO1, SO2 are necessary at the output of the drive-signal generation circuit 112. Depending on which of the electrodes has been selected as a reference electrode and as a measuring electrode, respectively, the input-side and the output-side switches of the drive-signal generation circuit 112 are adjusted.

If the signal of the measuring electrode does not lie within within the predetermined range, the respective switch will be opened and the switch SIgnd will be closed so that the reference potential of the measurement sensor 100 is applied to the reference electrode 106.

The method according to the present invention which is used for equalizing a patient's potential with respect to medical equipment will now be described on the basis of the flow chart shown in FIG. 2.

Before the description of the flow chart a short a explanation of used variables is given below.

Bitcoded Electrode State Variables

All of the following variables consist of a predetermined number of bits corresponding to the number of electrodes used with the inventive system.

CBL_IOREQ .... determines whether an electrode is used as reference electrode (biti="0") or not (biti="1");

CBL_INOP .... determines whether an electrode works properly (biti="0") or is malfunctioning (biti="1");

CBL_VECUSE .... determines whether an electrode is used as measuring electrode by a regarded channel vector(s) (biti="1") or not (biti="0");

CBL_RLDIN .... determines whether an electrode is used as RLD input (biti="1") or not (biti="0");

Prior to the first execution of the routine the variable CBL_IOREQ is set according to the used electrodes by a high level application resisting outside the device 100.

The routine is at predetermined times periodically executed.

The routine is started at step S1.

In step S2, the operation INOP_EVAL is carried out, which checks the electrodes and their signal. For malfunctioning electrodes the corresponding bits in the variable CBL_INOP are set to "1" (biti="1").

In step S3, the operation VECUSE_EVAL is carried out, which determines electrodes being used by the regarded channel vector. For the determined electrodes the corresponding bits in the variable CBL_VECUSE are set to "1" (biti="1").

In step S4 the variable CBL_RLDIN is determined by a logical AND of CBL_IOREQ and the complement of CBL_INOP, wherein the bits in CBL_IOREQ corresponding to reference electrodes are set to "0" (biti="0").

In step S5, it is determined whether CBL_RLDIN equal zero, that is whether there are any "good" non-reference electrodes.

If it is determined that CBL_RLDIN does not equal zero the routine proceeds to step S6.

In step S6, a new value of the variable CBL_RLDIN is determined by a logical AND of CBL_RLDIN and CBL_VECUSE.

In step S7, it is determined whether the newly determined value of CBL_RLDIN equal zero, that is whether there are any "good" measuring electrodes.

If it is determined that CBL_RLDIN does not equal zero all "good" measuring electrodes are used as RLD input and the routine proceeds to step S8.

In step S8, the variable CBL_IOREQ is applied to SOi, that is the switches corresponding to the reference electrodes are closed. Further the variable CBL_RLDIN is applied to SIi, that is the switches corresponding to the measuring electrodes being used as RLD input are closed.

At step S9 the routine ends.

If it is in step S5 determined that CBL_RLDIN does equal zero the routine proceeds to step S10.

In step S10 the variable CBL_RLDIN is set to SIgnd, that is the switch SIgnd is closed thus employing the already described passive equalization. The routine proceeds then to step S8.

If it is in step S7 determined that the newly determined value of CBL_RLDIN does equal zero the routine proceeds to step S11.

In step S11 a new value of the variable CBL_RLDIN is determined by a logical AND of CBL_IOREQ and the complement of CBL_INOP, that is the "good" non-reference electrodes are used as RLD input. The routine proceeds then to step S8.

Figure 3:
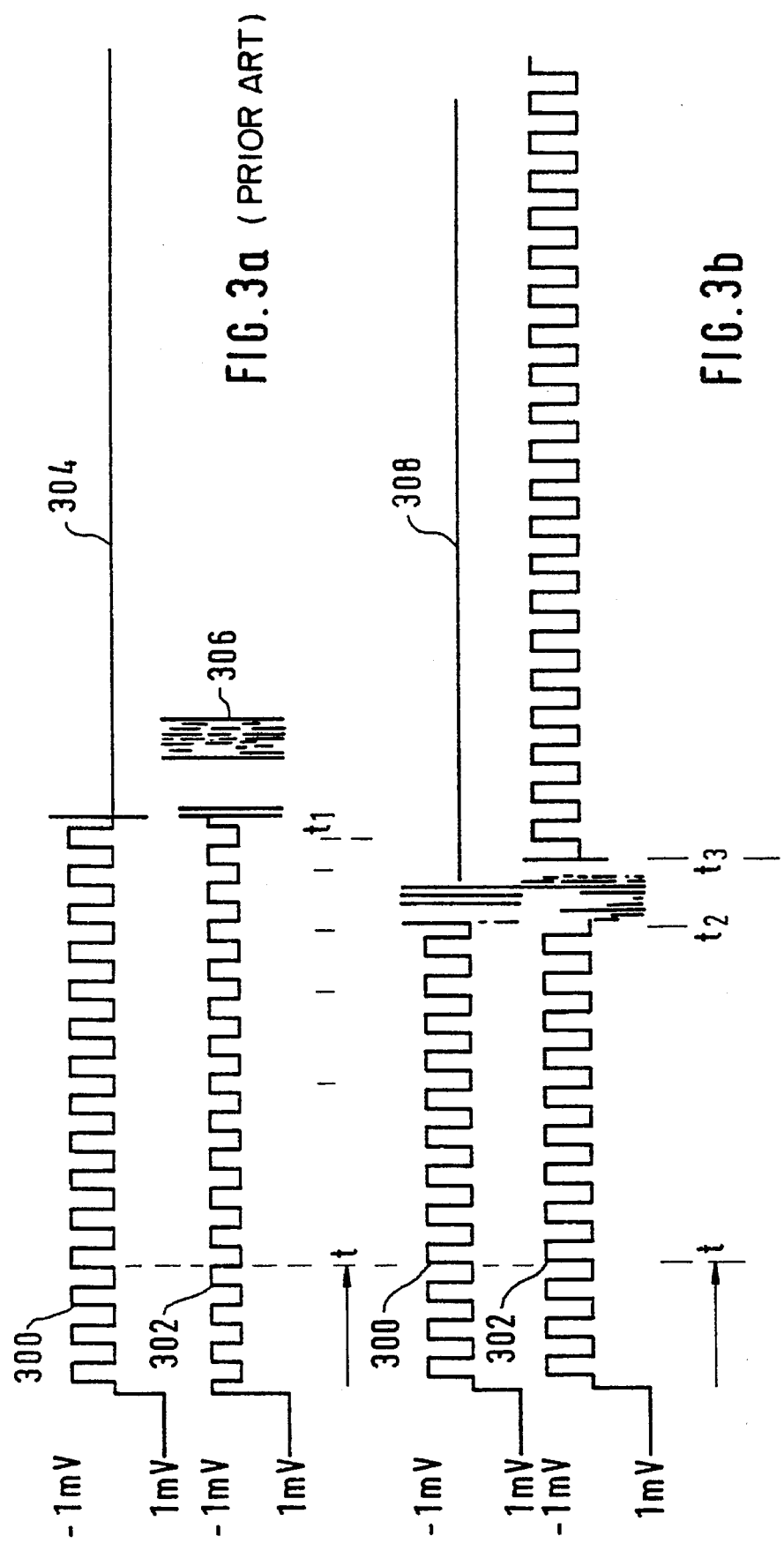
FIG. 3a shows a signal waveform of two channels, which will occur in a device according to the prior art when one electrode loosens.
FIG. 3b shows a signal waveform of two channels, which will occur in the device according to the present invention when one electrode loosens.
Figure 4:
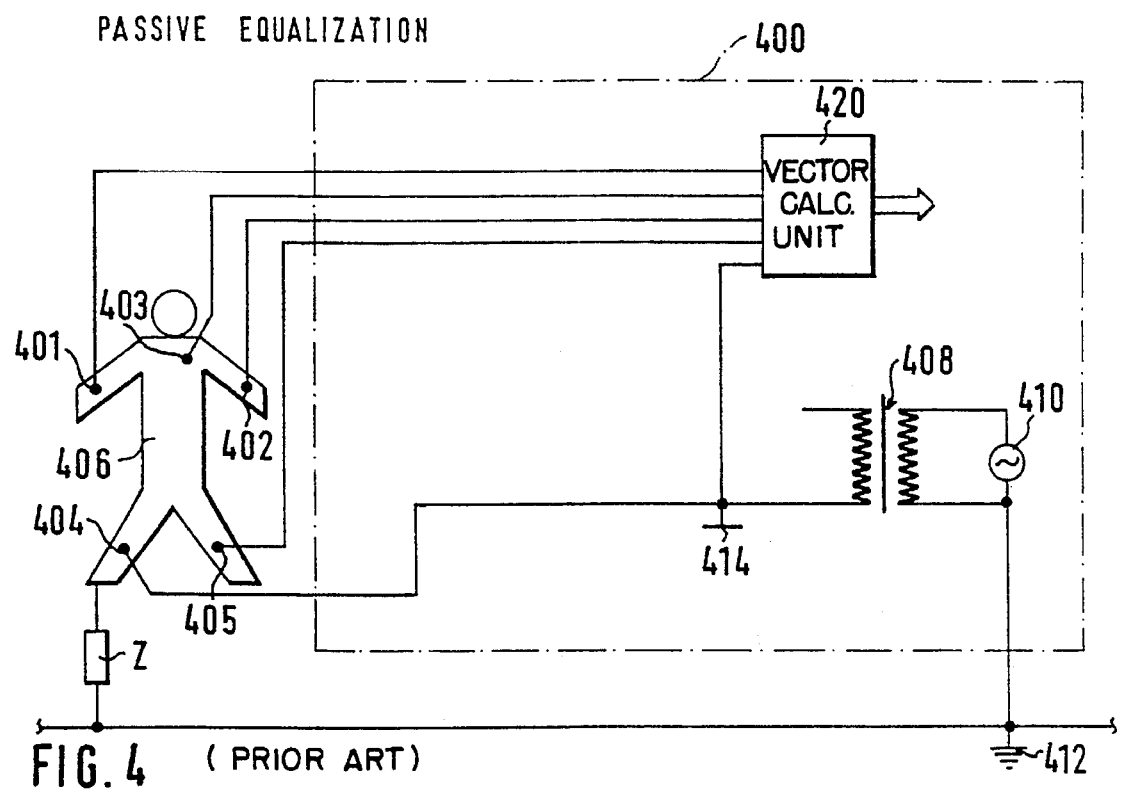
FIG. 4 shows an electrocardiogram measuring instrument using a passive equalization according to the prior art.
Figure 5:
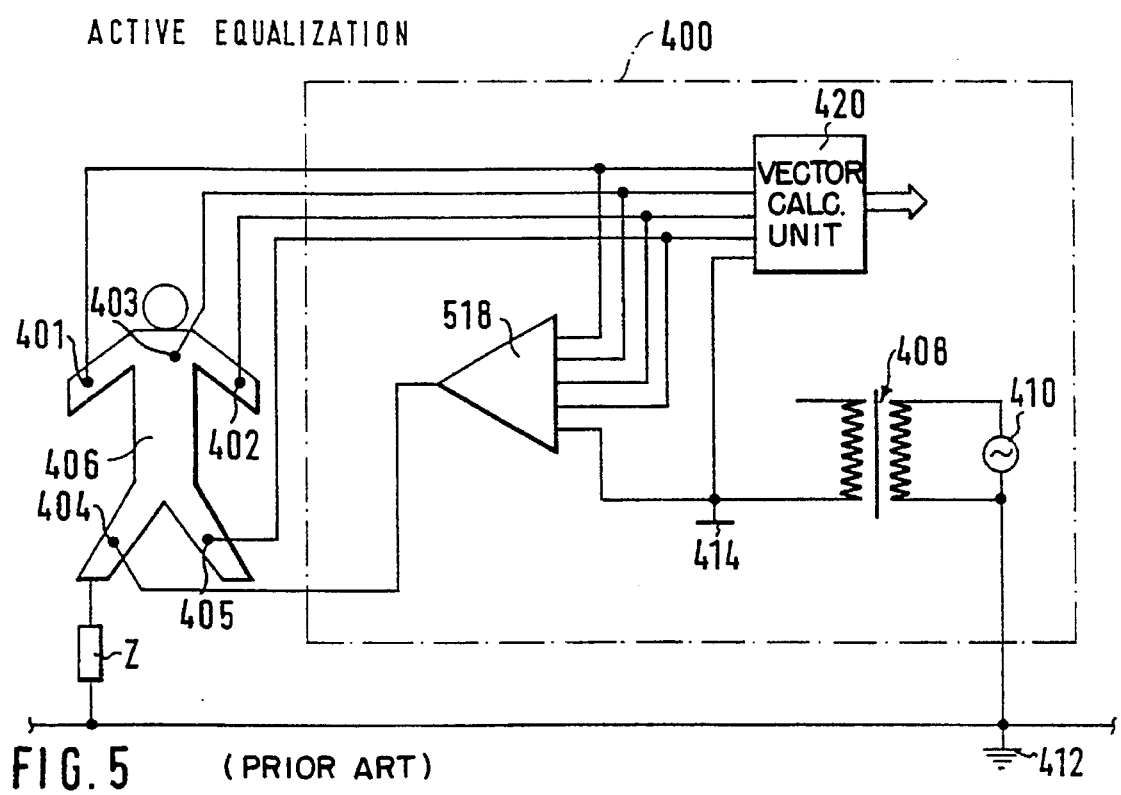
FIG. 5 shows an electrocardiogram measuring instrument using an active equalization according to the prior art.

In FIG. 3, the signal waveforms of two respective channels are shown; the signal waveform in FIG. 3a has already been explained in the introduction to the specification and is only shown together with the signal waveform in FIG. 3b for demonstrating the improvement achieved by the present invention in comparison with the prior art.

Also FIG. 3b shows a first signal 300 and a second signal 302, which correspond to the signals described in FIG. 3a. The first signal 300 corresponds to a first channel consisting of the measuring signals of a first measuring electrode and of a second measuring electrode, whereas the signal waveform 302 corresponds to a second channel consisting of the measuring signals of a first and of a third electrode.

At a moment t2, the second measuring electrode loosens, and this will have the effect that a signal will no longer be received in the first channel in section 308.

In order to avoid the problems described in connection with the signal waveforms shown in FIG. 3a, the control circuit of the device according to the present invention is effective so as to prevent disturbances from being coupled into the second channel 302.

The control circuit detects that the measuring signal of the second measuring electrode (the measuring electrode which was separated) no longer lies within a predetermined range, and, consequently, it will open the switch which applies the measuring signal of the second measuring electrode to the drive-signal generation circuit so that the disturbance coupled in by the second measuring electrode will be suppressed after a short period of time at the moment t3, and thus it will be possible to continue the reception of the signal in channel 2.

The disturbances are coupled in only for the short period of time between t2 and t3. The length of the period of time depends on how rapidly the device according to the present invention detects that the measuring signal of the second measuring electrode no longer lies within the predetermined range, and on how rapidly the device according to the present invention excludes the measuring signal of the second measuring electrode by opening the relevant switch.

It is noted that the detection that the measuring signals of the measuring electrodes lie within a predetermined range also includes the detection of disturbed measuring signals.

The detection of disturbed signals includes the detection of so called line frequency interferences, that is the coupling of mains frequencies, or strong changes or fluctuations of d.c. components, that is a d.c. drift.

Figure 2:
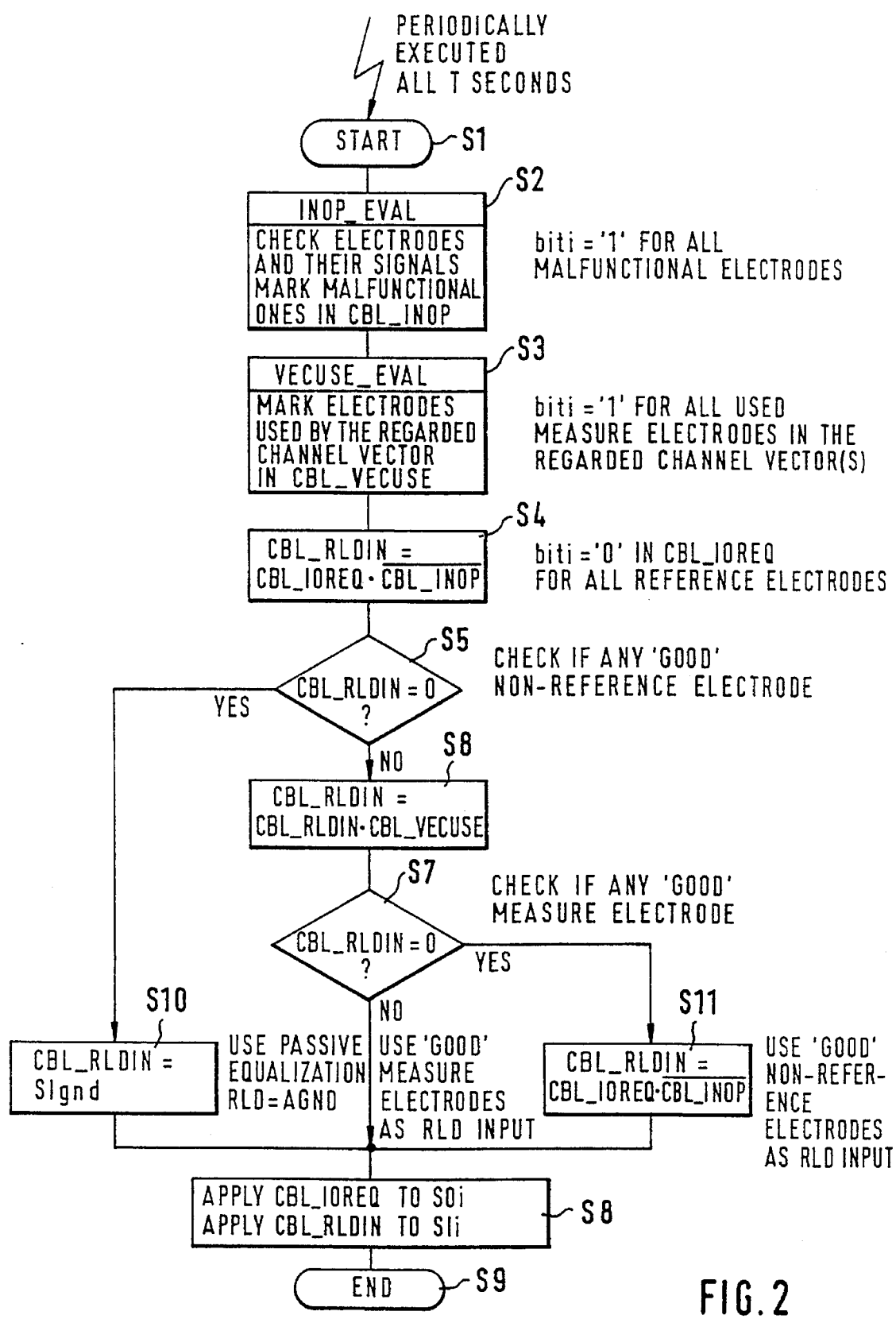
FIG. 2 shows a flow chart representative of one embodiment of the method according to the present invention.

The above described disturbances may be used as an indication of a "bad" connection of the electrodes to the patient, which can already be observed by the CPU prior to the detection of malfunctioning electrodes (FIG. 2, step S2), that is prior to the execution of the with reference to FIG. 2 described routine.

I claim:

1. A device for equalizing a patient's potential with respect to medical equipment, comprising:

a measuring electrode and a reference electrode, which are adapted to be applied to the patient;

a drive-signal generation circuit having an input and an output, wherein said output is connected to the reference electrode; and a control circuit which has supplied thereto a measuring signal from said measuring electrode and which examines whether said measuring signal lies within a predetermined range, said control circuit supplying the measuring signal to the input of the drive-signal generation circuit if said measuring signal lies within a predetermined range; and said control circuit applying a reference potential to the input of the drive-signal generation circuit if said measuring signal does not lie within said predetermined range.

2. A device for equalizing a patient's potential with respect to medical equipment, comprising:

at least two measuring electrodes and one reference electrode which are adapted to be applied to the patient;

a drive-signal generation circuit having a plurality of inputs and an output, wherein said output is connected to the reference electrode;

a control circuit which has supplied thereto measuring signals from said measuring electrodes and which examines whether said measuring signals lie within a predetermined range;

said control circuit supplying only those measuring signals to the plurality of inputs of the drive-signal generation circuit which lie within a predetermined range; and said control circuit applying a reference potential to one of said plurality of inputs of the drive-signal generation circuit if the measuring signals do not lie within said predetermined range.

3. A device according to claim 2, which additionally comprises a device combining the measuring signals so as to form a vector for defining thus a channel, the control circuit supplying to said drive-signal generation circuit only measuring signals which are included in said vector.

4. A device according to claim 2, wherein the drive-signal generation circuit includes at least two input side switches connected to said plurality of inputs by means of which the measuring signals can selectively be supplied to the inputs of said drive-signal generation circuit;

the control circuit comprises an analog-to-digital converter, a central processing unit and a switch control means for controlling said at least two input-side switches;

said analog-to-digital converter being connected to the measuring electrodes and the reference electrode and, via a first signal bus, to the central processing unit;

the central processing unit being connected via a second signal bus to the switch control means, which, in turn, switches the input-side switches in response to control signals received from the central processing unit.

5. A device according to claim 4 wherein the drive-signal generation circuit includes an input-side reference potential switch by means of which a reference potential can be applied to said drive-signal generation circuit.

6. A method for equalizing a patient's potential with respect to medical equipment, comprising the following steps:

applying a measuring electrode and a reference electrode to the patient;

examining whether a measuring signal supplied by the measuring electrode lies within a predetermined range;

producing a drive signal, which is supplied to the reference electrode, on the basis of the measuring signal, if said measuring signal lies within said predetermined range; and applying a reference potential to the reference electrode, if said measuring signal does not lie within said predetermined range.

7. A method for equalizing a patient's potential with respect to medical equipment, comprising the following steps:

applying at least two measuring electrodes and a reference electrode to the patient;

examining whether measuring signals supplied by the measuring electrodes lie within a predetermined range;

producing a drive signal, which is supplied to the reference electrode, only on the basis of the measuring signals which lie within said predetermined range; and applying a reference potential to the reference electrode, if the measuring signals do not lie within said predetermined range.

* * * * *